United States Patent [19]
Guadliana et al.

[11] Patent Number: 6,074,855
[45] Date of Patent: Jun. 13, 2000

[54] PROCESS FOR PREPARING SPIROLAXINE AND SPIROLAXINE METHYL ETHER

[75] Inventors: Mark A. Guadliana, Stonington; Liang H. Huang, East Lyme; Takushi Kaneko, Guilford, all of Conn.

[73] Assignee: Pfizer Inc., New York, N.Y.

[21] Appl. No.: 08/894,088

[22] PCT Filed: Mar. 30, 1995

[86] PCT No.: PCT/IB95/00217
§ 371 Date: Aug. 13, 1997
§ 102(e) Date: Aug. 13, 1997

[87] PCT Pub. No.: WO96/30538
PCT Pub. Date: Oct. 3, 1996

[51] Int. Cl.[7] .............................. C12P 17/04; C12N 1/14; A01N 43/16; C07D 307/77
[52] U.S. Cl. ...................... 435/126; 435/254.1; 514/451; 549/297
[58] Field of Search ..................................... 435/123, 126, 435/254.1; 549/200, 263, 295, 297; 514/449, 461, 462

[56] References Cited

PUBLICATIONS

ATCC Catalogue of Filamentous Fungi (1991) 18th edition, pp. 105, 303, 304, 392.
Arnone et al., Phytochemistry, 1990, 29, No. 2, pp. 613–616.
Centraalbureau Voor Schimmelcultures, Delft 'List of Cultures 1987', 1987, Institute of the Royal Netherlands Academy of Arts and Sciences, Baarn, NL see pp. 76, 238, and 301.
O'Conner, H.J., Postgraduate Medical Journal, 1992, 68, 549–57.

*Primary Examiner*—Jean C. Witz
*Assistant Examiner*—Susan Hanley
*Attorney, Agent, or Firm*—Peter C. Richardson; Gregg C. Benson; Robert T. Ronau

[57] ABSTRACT

Processes for preparing spirolaxine and spirolaxine methyl ether, the compounds of formulas (I) and (II) respectively,

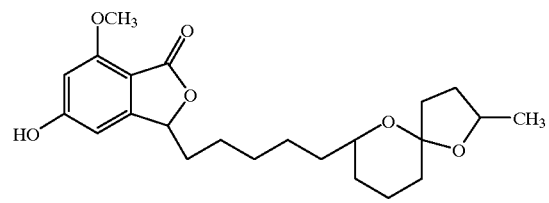

(I)

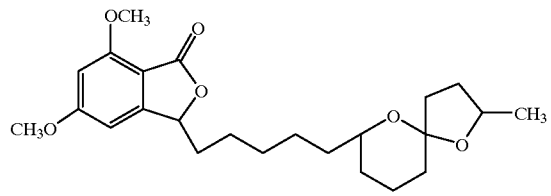

(II)

comprising fermenting fungi selected from the group consisting of *Sporotrichum pruinosum* FD 29585, ATCC 74327; *Sporotrichum pruinosum* FD 29454, ATCC 74329; *Sporotrichun pruinosum* FD 29586, ATCC 74328; and *Phanerochaete chrysosporiun* LN 3576, ATCC 74326. This invention also relates to a process for preparing spirolaxine comprising fermenting *Sporotrichum pruinosum* FD 29458, ATCC 74330.

13 Claims, No Drawings

PROCESS FOR PREPARING SPIROLAXINE AND SPIROLAXINE METHYL ETHER

CROSS-REFERENCE TO RELATED APPLICATIONS

This application is the National Stage of copending International Application PCT/IB95/00217, filed Mar. 30, 1995, entitled "Process for Preparing Spirolaxine and Spirolaxine Methyl Ether".

BACKGROUND OF THE INVENTION

This invention relates to processes for producing the compound of formula (I)

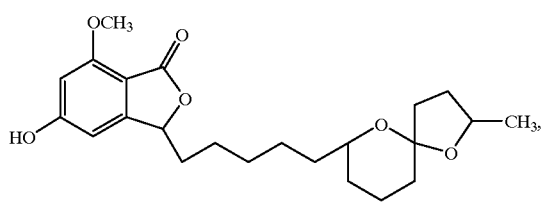

(hereinafter referred to as spirolaxine); and to processes for producing the compound of formula (II)

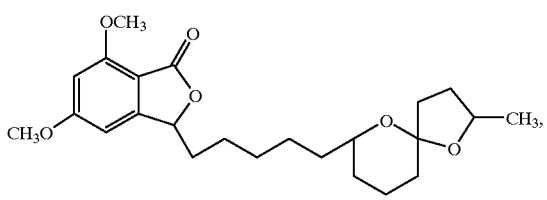

(hereinafter referred to as spirolaxine methyl ether).

Spirolaxine is a known antibiotic which can be isolated from the fungus *Chrysosporium pruinosum* ATCC 15155. Spirolaxine is reported to have weak bacteriostatic activity against *Bacillus cereus, Bacillus subtillis* and *Escherichia coli*. Arnone et al., Phytochemistry, 1990, 29, 613–616. Further, spirolaxine is reported to have no antifungal activity against *Aspergillus niger, Botrytis cinerea, Cladosporium, cucumerinum, Ophiostoma ulmi* and *Saccharomyces cerevisiae*. Arnone et al., Phytochemistry, 1990, 29, 613–616.

Gastric and duodenal ulcers affect a significant portion of the human population worldwide. Currently, the usual treatment for both gastric and duodenal ulcers involves treatment of the patient with $H_2$ blockers. While generally effective in healing ulcers, ulcer relapse occurs in up to 90% of patients within a year of discontinuing $H_2$ blocker therapy. O'Connor, H. J., Postgraduate Medical Journal, 1992, 68, 549–57. Thus, patients must continue the treatment for many years or risk a recurrence of the ulcer. It is now known that ulcer healing drugs such as colloidal bismuth subcitrate (CBS) are helicobactericidal and as such CBS is used in combination with $H_2$ blockers to treat ulcers. O'Connor, ibid. Additionally, CBS, an $H_2$ blocker and amoxicillin have been used in combination to treat ulcer patients. O'Connor, ibid.

*Helicobacter pylori* has recently been demonstrated to be a major causative agent in gastric and duodenal ulcers and other gastroduodenal disorders, diseases and adverse conditions. Thus, antibiotic therapy to eliminate *Helicobacter pylori* from the gastroduodenal tract would remove the root cause of said gastroduodenal disorders, diseases and adverse conditions and eliminate the need for an ulcer patient to continue long and costly treatment with $H_2$ blockers and the like. None of the foregoing treatments are capable of 100% eradication of *Helicobacter pylori*.

Spirolaxine and spirolaxine methyl ether are potent helicobactericidal compounds, as disclosed hereinbelow. A helicobactericidal compound is a compound which kills *Helicobacter pylori*. Therefore spirolaxine and spirolaxine methyl ether possess utility in treating gastroduodenal disorders, diseases and adverse conditions and particularly in treating gastric and duodenal ulcer and preventing gastric cancer.

It has now been found that spirolaxine and spirolaxine methyl ether are produced by various strains of fungi belonging to the genera Sporotrichum and Phanerochaete.

SUMMARY OF THE INVENTION

This invention is directed to a process for preparing the compound of formula (I)

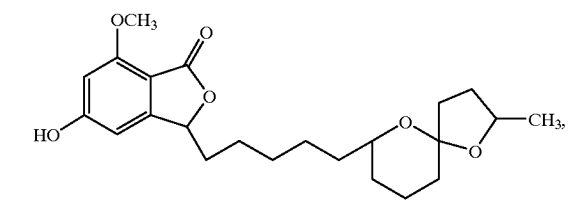

comprising fermenting a culture of a fungus selected from the group consisting of *Sporotrichum pruinosum* FD 29585, ATCC 74327; *Sporotrichum pruinosum* FD 29454, ATCC 74329; *Sporotrichum pruinosum* FD 29586, ATCC 74328; *Sporotrichum pruinosum* FD 29458, ATCC 74330; and *Phanerochaete chrysosporium* LN 3576, ATCC 74326; and isolating said compound of formula (I).

This invention is also directed to a process for preparing the compound of formula (II)

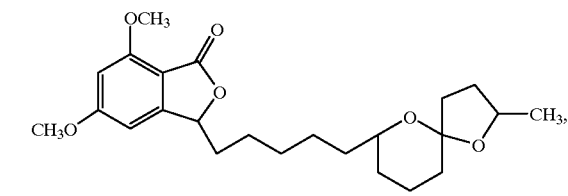

comprising fermenting a culture of a fungus selected from the group consisting of *Sporotrichum pruinosum* FD 29585, ATCC 74327; *Sporotrichum pruinosum* FD 29454, ATCC 74329; *Sporotrichum pruinosum* FD 29586, ATCC 74328; and *Phanerochaete chrysosporium* LN 3576, ATCC74326; and isolating said compound of formula (II).

With respect to the compounds of formula (I) and (II) prepared by the process of this invention, it is to be understood that there are numerous stereoisomeric forms of said compounds such as optical isomers due to the presence of four asymmetric carbon atoms in each of said compounds and that said stereoisomeric forms are also included within the scope of the process of this invention.

DETAILED DESCRIPTION OF THE INVENTION

The present invention is readily carried out. Thus, the compounds of formulas (I) and (II) hereinabove are prepared by fermentation of the fungi recited hereinabove and subsequent isolation from the fermentation broth.

The fungi which are used in the process of this invention were deposited in lyophilized form with the American Type Culture Collection, 10801 University Boulevard Manassas Va., 20110-2209 U.S.A., under the terms of the Budapest Treaty on Feb. 17, 1995. All restrictions on the availability to the public of the fungus cultures so deposited will be irrevocably removed upon the issuance of a patent from this specification. The fungi which were so deposited are *Sporotrichum pruinosum* FD 29585 (ATCC 24782), *Sporotrichum pruinosum* FD 29454 (ATCC 16498), *Sporotrichum pruinosum* FD 29586 (ATCC 36374), *Sporotrichum pruinosum* FD 29458 (IMI 302923) and *Phanerochaete chrysosporium* LN 3576 (FPL 11894). The ATCC gave these newly deposited fungi new accession numbers ATCC 74327, ATCC 74329, ATCC 74328, ATCC 74330, and ATCC 74326, respectively. All restrictions on the availability to the public of the fungus cultures so deposited will be irrevocably removed upon the issuance of a patent from this specification.

The fungi used in the process of this invention can be obtained from the merican Type Culture Collection (ATCC). Descriptions of the Sporotrichum cultures are found in Stalpers, J. A., Studies in Mycology, 1984, 24, 105, which discloses the morphological and physiological characteristics of members of Sporotrichum used in the process of this invention. A description of the Phanerochaete species used in the process of this invention is found in Burdsall, H. H. Jr., Mycol. mem., 1985, 10, 165.

The fungi used in the process of this invention are readily fermented to provide a fermentation broth containing spirolaxine and spirolaxine methyl ether. Cultivation of the fungal culture used in this invention preferably takes place in aqueous nutrient media or on solid media at a temperature of 25 to 30° C., and under stationary aerobic conditions or submerged aerobic conditions with agitation. Nutrient media which are useful for such purposes include a source of assimilable carbon such as sugars, starch and molasses; and a source of organic nitrogen such as casein, enzymatic digests of casein, soybean meal, cottonseed meal, peanut meal and wheat gluten. A source of growth substances such as grain solubles, fish meal and yeast extract as well as salts such as sodium chloride and calcium carbonate and trace minerals such as iron, magnesium, zinc, cobalt and manganese may also be utilized with advantageous results. If excessive foaming is encountered during fermentation, anti-foam agents such as vegetable oils or silicones may be added to the fermentation medium. Aeration of the medium in tanks for submerged growth is preferably maintained at the rate of about 0.5 to 2 volumes of free air per volume of broth per minute. Agitation may be maintained by means of agitators well known to those in the field of fermentation. Aseptic conditions must, of course, be maintained throughout the transfer of the fungus and its growth period.

The fungus is grown on slants on a suitable growth medium such as potato dextrose agar (PDA) for a sufficient period of time to obtain a profuse culture on the growth medium. Generally 4 days to about 21 days are required to obtain sufficient growth to proceed. The slants thus obtained are washed with distilled water and the suspensions thus obtained are homogenized for a sufficient length of time that the homogenate is easily transferable. The homogenate is inoculated into an aqueous nutrient medium in a suitable fermentor, such as shake flasks, Roux bottles, Fernbach flasks or the like. The fermentor is shaken at about 200 rpm and a temperature of from about 24° C. to about 30° C. for about 2 days to about 20 days. This procedure provides a fermentation broth which contains spirolaxine and spirolaxine methyl ether. The fungus may also be cultivated on bioassay plates which are filled with 225 milliliters of aqueous media containing 20 grams of agar per liter. The washed suspension is spread over the surface of the agar and the plates are incubated at 24° C. and 85% humidity in an incubator. After 21 to 24 days of incubation, the growth is scraped off the plates and the compound of formula (I) and the compound of formula (II) are extracted.

Spirolaxine and spirolaxine methyl ether are isolated from the fermentation broth by extraction of the broth with a suitable organic solvent in which spirolaxine and spirolaxine methyl ether readily dissolve. Thus, the broth is extracted with a suitable extraction solvent such as chloroform, methyl isobutyl ketone, dichloromethane, ethyl acetate, or a solvent system such as ethyl acetate containing 1% methanol. The residue obtained after extraction is partitioned between hexane and acetonitrile and the acetonitrile layer is collected and concentrated to yield a residue which is chromatographed according to the standard methods of organic chemistry well known to one of ordinary skill in the art to afford spirolaxine and spirolaxine methyl ether.

The compound of formula (I) and the compound of formula (II) thus prepared are useful in the treatment of gastric ulcer, duodenal ulcer and gastric cancer. For use in the treatment of conditions of gastric ulcer, duodenal ulcer and gastric cancer in a mammal, including man, an effective amount of a compound of formula (I) or the compound of formula (II) is formulated into a suitable pharmaceutical composition. Depending upon the potency of the particular compound of formula (I) or formula (II) being administered, about 1 mg/kg of body weight per day to about 100 mg/kg of body weight per day, in single or multiple daily doses, is administered to the mammal being treated. A more preferred range is 10 mg/kg of body weight per day to about 40 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is complicated by the patient's inability to ingest the drug.

The compound of formula (I) and the compound of formula (II) may also be administered in combination with a suitable $H_2$ blocker such as, but not limited to, ranitidine, cimetidine, famotidine, or izatidine or a proton pump inhibitor such as, but not limited to omeprazole. For use in the treatment of conditions of gastric ulcer, duodenal ulcer and gastric cancer in a mammal, including man, an effective amount of a combination of a compound of formula (I) or the compound of formula (II) and said $H_2$ blocker or said proton pump inhibitor are formulated into a suitable pharmaceutical composition. Depending upon the potency of the combination of the particular compound of formula (I) or formula (II) and said $H_2$ blocker or said proton pump inhibitor being administered, about 1 mg/kg of body weight per day to about 100 mg/kg of body weight per day of the compound of formula (I) or formula (II) along with about 0.1 mg/kg of body weight per day to about 5.0 mg/kg of body weight per day of said $H_2$ blocker or said proton pump inhibitor is administered, in single or multiple daily doses, to the mammal being treated. A more preferred range is 10 mg/kg of body weight per day to about 40 mg/kg of body weight per day of the compound of formula (I) or formula (II) and 0.5 mg/kg of body weight per day to about 3.0 mg/kg of body weight per day of said $H_2$ blocker or proton pump inhibitor, although in particular cases, at the discretion of the attending physician, doses outside the broader range may be required. For example, when said $H_2$ blocker is cimetidine, the preferred dosage for an average, 70 kg adult, is 800 mg twice a day or 1600 mg once a day, at bedtime. The preferred route of administration is generally oral, but parenteral administration (e.g., intravenous, intramuscular, subcutaneous or intramedullary) will be preferred in special cases such as where oral administration of this combination is complicated by the patient's inability to ingest the drug.

The compound of formula (I) and the compound of formula (II) may also be administered in combination with a suitable $H_2$ blocker such as, but not limited to, ranitidine, cimetidine, famotidine, or izatidine or a proton pump inhibitor such as, but not limited to omeprazole, and colloidal bismuth subcitrate. For use in the treatment of conditions of gastric ulcer, duodenal ulcer and gastric cancer in a mammal, including man, an effective amount of a combination of a compound of formula (I) or the compound of formula (II), said $H_2$ blocker or said proton pump inhibitor, and colloidal bismuth subcitrate are formulated into a suitable pharmaceutical composition. Depending upon the potency of the combination of the particular compound of formula (I) or formula (II), said $H_2$ blocker or said proton pump inhibitor, and said colloidal bismuth subcitrate being administered, about 1 mg/kg of body weight per day to about 100 mg/kg of body weight per day of said compound of formula (I) or formula (II) along with about 0.1 mg/kg of body weight per day to about 5.0 mg/kg of body weight per day of said $H_2$ blocker or said proton pump inhibitor and about 14 mg/kg of body weight per day to about 56 mg/kg of body weight per day of colloidal bismuth subcitrate is administered, in single or multiple daily doses, to the mammal being treated. A more preferred range is 10 mg/kg of body weight per day to about 40 mg/kg of body weight per day of the compound of formula (I) or formula (II), 0.5 mg/kg of body weight per day to about 3.0 mg/kg of body weight per day of said $H_2$ blocker or said proton pump inhibitor and 14 mg/kg of body weight per day to about 28 mg/kg of body weight per day of said colloidal bismuth subcitrate, although in particular cases, at the discretion of the attending physician, doses outside the broader range may be required. The preferred route of administration of this combination is generally oral, but parenteral administration (e.g., intravenous, intramuscular, subcutaneous or intramedullary) will be preferred in special cases such as where oral administration is complicated by the patient's inability to ingest the drug.

The compound of formula (I) and the compound of formula (II) may also be administered in combination with a suitable $H_2$ blocker such as, but not limited to, ranitidine, cimetidine, famotidine, or izatidine or a proton pump inhibitor such as, but not limited to omeprazole, and an antibiotic such as, but not limited to amoxicillin and tetracycline. For use in the treatment of conditions of gastric ulcer, duodenal ulcer and gastric cancer in a mammal, including man, an effective amount of a combination of a compound of formula (I) or the compound of formula (II), said $H_2$ blocker or said proton pump inhibitor and said antibiotic are formulated into a suitable pharmaceutical composition. Depending upon the potency of the combination of the particular compound of formula (I) or formula (II), said $H_2$ blocker or said proton pump inhibitor and said antibiotic being administered, about 1 mg/kg of body weight per day to about 100 mg/kg of body weight per day of said compound of formula (I) or formula (II) along with about 0.1 mg/kg of body weight per day to about 5.0 mg/kg of body weight per day of said $H_2$ blocker or said proton pump inhibitor and about 7 mg/kg of body weight per day to about 28 mg/kg of body weight per day of antibiotic is administered, in single or multiple daily doses, to the mammal being treated. A more preferred range is 10 mg/kg of body weight per day to about 40 mg/kg of body weight per day of the compound of formula (I) or formula (II), 0.5 mg/kg of body weight per day to about 3.0 mg/kg of body weight per day of said $H_2$ blocker or said proton pump inhibitor and 14 mg/kg of body weight per day to about 28 mg/kg of body weight per day of said antibiotic, although in particular cases, at the discretion of the attending physician, doses outside the broader range may be required. The preferred route of administration of this combination is generally oral, but parenteral administration (e.g., intravenous, intramuscular, subcutaneous or intramedullary) will be preferred in special cases such as where oral administration is complicated by the patient's inability to ingest the drug.

Spirolaxine and spirolaxine methyl ether are generally administered in the form of a pharmaceutical composition comprising at least one of spirolaxine or spirolaxine methyl ether together with a pharmaceutically acceptable vehicle or diluent. Such compositions are generally formulated in a conventional manner utilizing solid or liquid vehicles or diluents as appropriate to the mode of administration.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

The utility of the compounds of the present invention as medicinal agents in the treatment of gastroduodenal disorders such as gastric ulcers, duodenal ulcers or gastric cancer is demonstrated by the activity of said compounds against *Helicobacter pylori* in the in vitro biological screens described hereinbelow. Said screens also provide a means whereby the activities of the compound of formula (I) and the compound of formula (II) can be compared with the activities of other known compounds and treatments. The results of these comparisons are useful for determining dosage levels in mammals, including man, for the treatment of gastroduodenal disorders such as gastric ulcers, duodenal ulcers or gastric cancer.

The compound to be evaluated is solubilized in dimethylsulfoxide (DMSO) and diluted with a sterile brucella broth. Brucella broth is a mixture of pancreatic digest of casein (10 grams), peptic digest of animal tissue (10 grams), yeast extract (2 grams), sodium chloride (5 grams), dextrose (1 gram), sodium bisulfite (0.1 gram) and agar (15 grams) and can be purchased from Acumedia Manufacturers, Inc., Baltimore, Md., 21211, USA. The solubility is noted. The final concentration of dimethylsulfoxide is about 10% of the total volume. Serial two-fold dilutions using an equivalent amount of test compound and brucella broth are then made into sterile brucella broth. An aliquot of each broth dilution within the series is placed in separate sterile petri dishes. Brucella agar, supplemented with about 7% horse blood, is melted and cooled to about 50° C. and then added to the petri dishes such that the final concentration of test compound in the agar is 1:10 and the final concentration of DMSO in the agar is 1%. The agar plates can be prepared and refrigerated overnight one day prior to inoculation with *Helicobacter pylori*.

*Helicobacter pylori* cultures are maintained on trypticase soy-5% sheep blood agar plates, and are transferred every 48 hours. *Helicobacter mustelae* cultures are maintained on the same agar, and are transferred every 48–60 hours, depending upon the heaviness of the growth of the previous transfer. Plates are incubated at 37° C. in GasPak (Becton Dickinson Microbiology Systems, Cockeysville, Md., 21030, USA) jars with CampyPak Plus (Becton Dickinson Microbiology Systems, Cockeysville, Md., 21030, USA) envelopes with palladium catalyst.

*Helicobacter pylori* cultures are grown in brucella broth supplemented with 10% fetal calf serum in deep petri dishes. The plates are incubated for 18–20 hours at 37° C. in GasPak jars with water-activated CampyPak Plus envelopes with palladium catalyst on a shaker at 50 rpm.

Overnight cultures are diluted ten-fold in brucella broth (no FCS) in screw-capped tubes for use as the standard inoculum. The wells of a Steere's replicator (Craft Machine, Inc., I-95 and Concord Road, Chester, Penn., 19203, USA) are filled with the diluted organism and cells are placed on the agar surface. Inoculated plates are placed in a GasPak jar to which water-activated CampyPak Plus envelopes with palladium catalyst have been added. The jars are incubated at 37° C. for 48 hours. Following incubation, all test plates are compared to a compound-free growth control plate. The minimum inhibitory concentration (MIC) is the concentration which inhibits growth compared to the control plate. A thin film of growth might be visible at higher concentrations but this is discounted, and is not considered to be the true MIC. Control organisms are also inoculated on each plate, and these are diluted 1000-fold for use as inocula. The control organisms include *Campylobacter jejuni*, and the 536G screening cultures of *Escherichia coil, Enterobacter aerogenes, Escherichia cloacae, Providencia stuartii* and *Providencia rettgeri*. Plates and/or inocula transfers are not kept out of a $CO_2$ atmosphere for longer than two hours. All manipulations involving Helicobacter cultures are performed in a laminar flow hood to decrease the chance of contamination of the cultures with mold.

The microdilution broth method described in the Manual of Clinical Microbiology, 4th Edition, E. H. Lennette et al., eds., American Society for Microbiology, Washington, D.C., 1985, pages 973–4 is also used to determine the minimum inhibitory concentration (MIC) of the test compounds.

The abbreviations PDA, MEA, CM, DMSO and FCS, where used herein, mean potato dextrose agar, malt extract agar, corn meal, dimethylsulfoxide and fetal calf serum, respectively. Where used hereinabove and in the claims, the term "mammal" is understood to embrace the term "human."

The present invention is illustrated by the following examples. However, it should be understood that the invention is not limited to the specific details of these examples.

EXAMPLE ONE

Liquid Fermentation

Ten to twenty-one day-old slants of a culture of *Sporotrichum pruinosum* FD 29585 (ATACC 74327) were grown on ATCC medium #336 (PDA) or Difco PDA. The slants were washed with 8 mL of sterile water, yielding a suspension. The suspensions were homogenized twice at 20 seconds each. One milliliter of these homogenized suspensions were inoculated into shake flasks, each containing 50 mL of MPG medium.

| KF Medium | |
|---|---|
| Corn Steep Liquor | 5 g |
| Tomato Paste | 40 g |
| Oat flour | 10 g |
| Glucose | 10 g |
| Trace element mix | 10 ml |
| Distilled Water | 1 liter |
| pH adjusted to 6.8 | |
| The trace element mix has the following composition: | |
| $FeSO_4.7H_2O$ | 1.0 g |
| $MnSO_4.4H_2O$ | 1.0 g |
| $CuCl_2.2H_2O$ | 0.025 g |
| $CaCl_2.2H_2O$ | 0.1 g |
| $H_3BO_3$ | 0.056 g |
| $(NH_4)_6Mo_7O_{24}.4H_2O$ | 0.0019 g |
| $ZnSO_4.7H_2O$ | 0.2 g |
| 0.6N HCl | 1 liter |

| MPG Medium | |
|---|---|
| Malt extract | 40 g/L |
| Peptone | 4 g |
| Glucose | 40 g |
| Distilled water | 1 liter |

The flasks were incubated at 28° C. on a shaker at 200 rpm. After three days of growth, the seed broths were blended twice at twenty seconds each. One mL of the homogenized suspensions were inoculated into shake flasks, each containing 50 mL of MPGA or KF medium plus one gram of agar per liter.

| MPGA Medium | |
|---|---|
| Malt extract | 40 g/L |
| Peptone | 4 g |
| Glucose | 40 g |
| Agar | 1 g |
| Distilled water | 1 liter |

The flasks were incubated at 28° C. on a shaker at 200 rpm. The fermented broths were extracted after 10 days of incubation. If large balls were produced by the fermentation, the flask contents were homogenized. An equal volume of ethyl acetate containing 1% methanol was added. The flask was put on the shaker for ten minutes. The mixture was then centrifuged for ten minutes at 3,000 rpm. The solvent was poured off and the mycelium and aqueous layer was reextracted with 50 mL of ethyl acetate containing 1% methanol. The mixture was put on the shaker for ten minutes and centrifuged for ten minutes. The organic layers were combined and concentrated to afford an oil.

EXAMPLE TWO

Using a procedure analogous to that described in Example One hereinabove, ten- to twenty-one day-old slants of *Sporotrichum pruinosum* FD 29454 (ATCC 74329) and *Sporotrichum pruinosum* FD 29586 (ATCC 74328) were grown and fermented for 11 and 9 days, respectively, to produce an oil containing spirolaxine and spirolaxine methyl ether.

EXAMPLE THREE

Using a procedure analogous to that described in Example One hereinabove, ten- to twenty-one day-old slants of *Sporotrichum pruinosum* FD 29458 (ATCC 74330) were grown and fermented for 8 days to produce an oil containing spirolaxine.

EXAMPLE FOUR

Solid Fermentation of *Phanerochaete chrysosporium* LN 3576

Preparation of seed: Liquid nitrogen vials of *Phanerochaete chrysosporium* LN 3576 (ATCC 74326) were revived onto slants of malt agar (15 g of malt extract, 20 g of agar and one liter of sterile distilled water). After ten days of incubation, each slant was washed with ten milliliters of sterile distilled water resulting in a mycelial suspension.

One liter flasks were charged with sixteen grams of oatmeal and 80 mL of F5 medium. Three flasks of each culture were inoculated with three milliliters of washed suspension per flask. The flasks were incubated without shaking for various periods, two to six weeks, at 26° C. and 80% humidity in an incubator.

| F5 Medium | |
|---|---|
| Glucose | 10 g |
| Glycerol | 30 g |
| Peptone | 5 g |
| NaCl | 2 g |
| Agar | 1 g |
| Deionized Water | 1 L |

After the appropriate incubation period, ethyl acetate containing 1% methanol (100 mL) was added to each flask. The solid mass was broken up with a spatula and the contents were mixed on a shaker for 0.5 hours. The organic solvent was separated and the combined extracts were evaporated to give a brown oil.

EXAMPLE FIVE

Identification of Spirolaxine and Spirolaxine Methyl Ether

The oily residue obtained in Example One and Example Two were separately redissolved in acetonitrile and analyzed by HPLC. Two sets of HPLC conditions were used. By comparison of the retention time and UV profile with authentic samples, the oil of each Example was found to contain spirolaxine and spirolaxine methyl ether. The ability of the fungi of this invention to produce spirolaxine and spirolaxine methyl ether is shown in Table I.

HPLC system #1.

Waters 990 HPLC unit. (Waters Corporation, 34 Maple Street, Milford, Mass. 01757-3696)

column—Zorbax SB CN 4.6×250 mm. (Obtained from MAC-MOD Analytical, Inc., 127 Commons Court, P.O. Box 2600, Chadds Ford, Pa. 19317-9961)

particle size =5 $\mu$m guard cartridge—Zorbax SB CN 4.0×12.5 mobil phase—MeOH/$H_2O$ 65/35 premixed flow rate—1 mL/minute detection—UV 260 nm retention time for spirolaxine—7.6 minutes retention time for spirolaxine-methyl ether—10 minutes HPLC system #2.

Waters 996 Millennium HPLC unit column—Waters C 18 $\mu$-bondapak 3.9×300 particle size—10$\mu$m mobile phase—MeOH/$H_2O$ 70/30 flow rate—1 mL/minute detection—UV 260 nm retention time for spirolaxine—12.8 minutes retention time for spirolaxine-methyl ether—22 minutes

EXAMPLE SIX

Using a procedure analogous to that described in Example Five hereinabove, the oily residues obtained from Examples Two and Four were purified and identified. By comparison of the retention time and UV profile with authentic samples, each of these oils were found to contain spirolaxine and spirolaxine methyl ether, as shown in Table I hereinbelow.

EXAMPLE SEVEN

Using a procedure analogous to that described in Example Five hereinabove, the oily residue obtained from Example Three was purified and identified. By comparison of the retention time and UV profile with an authentic sample, the oil was found to contain spirolaxine, as shown in Table I hereinbelow.

| Culture Collection # | Organism | spirolaxine retention time (mins) | spirolaxine-methyl ether retention time (mins) | fermentation-solid/ liquid-time of HPLC | HPLC system |
|---|---|---|---|---|---|
| ATCC 74329 | *Sporotrichum pruinosum* FD 29454 | 7.58 | 10.27 | LIQ - 11 days | 1 |
| ATCC 74330 | *Sporotrichum pruinosum* FD 29458 | 7.46 | NONE | LIQ - 8 days | 1 |
| ATCC 74326 | *Phanerochaete chrysosporium* LN 3576 | 7.43 | 9.93 | SOL - 20 days | 1 |
| ATCC 74327 | *Sporotrichum pruinosum* FD 29585 | 7.41 | 9.93 | LIQ - 10 days | 1 |

| Culture Collection # | Organism | spirolaxine retention time (mins) | spirolaxine-methyl ether retention time (mins) | fermentation-solid/ liquid-time of HPLC | HPLC system |
|---|---|---|---|---|---|
| ATCC 74328 | *Sporotrichum pruinosum* FD 29586 | 7.66 | 10.14 | LIQ - 9 days | 1 |

Characterization:

1. Spirolaxine: mp 145° C.; $^1$HNMR (CDCl$_3$, δ) 1.16 (1H, dq), 1.25 (3H, d), 1.25 (1H, m), 1.29 (2H, m), 1.33 (1H, m), 1.39 (2H, m), 1.42 (1H, m), 1.42 (1H, m), 1.44 (1H, m), 1.55 (1H, bd), 1.65 (1H, m), 1.68 (2H, m), 1.72 (1H, m), 1.77 (1H, m), 1.82 (1H, m), 1.89 (1H, m), 1.92 (1H, m), 2.14 (1H, m), 3.73 (1H, m), 3.91 (3H, s), 4.17 (1H, ddq), 5.29 (1H, dd), 6.43 (1H, dd), 6.46 (1H, d): $^{13}$C NMR (CDCl$_3$, δ) 20.28, 21.21, 24.27, 25.28, 29.33, 30.81, 31.30, 33.55, 34.41, 35.97, 37.97, 55.84, 70.28, 73.91, 80.05, 99.20, 100.42, 105.98, 106.33, 155.11, 159.96, 164.14, 169.29; FABMS 405 m/e (M+H); EIMS 404.21626 m/e.

2. Spirolaxine methyl ether: $^1$HNMR (CDCl$_3$, δ) 1.16 (1H, dq), 1.25 (3H, d), 1.27 (1H, m), 1.32 (1H, m), 1.35 (2H, m), 1.41 (1H, m), 1.42 (1H, m), 1.43 (1H, m), 1.53 (1H, bd), 1.64 (1H, m), 1.67 (2H, m), 1.72 (1H, m), 1.74 (1H, m), 1.82 (1H, m), 1.87 (1H, m), 1.99 (1H, m), 2.14 (1H, m), 3.90 (3H, s), 3.96 (3H, s), 4.15 (1H, ddq), 5.30 (1H, dd), 6.40 (1H, dd), 6.42 (1H, d); $^{13}$C NMR (CDCl$_3$, δ) 20.40, 21.27, 24.55, 25.43, 29.35, 30.97, 31.37, 33.53, 34.79, 36.12, 38.01, 55.88, 55.97, 69.94, 73.64, 79.89, 97.40, 98.60, 106.03, 107.01, 155.18, 159.62, 166.65, 168.48; FABMS 419 m/e (M+H).

What is claimed is:

1. A process for preparing the compound of formula (I)

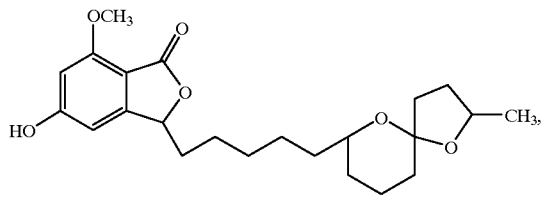

(I)

comprising fermenting a culture of a fungus selected from the group consisting of *Sporotrichum pruinosum* FD 29585 ATCC 74327, *Sporotrichum pruinosum* FD 29454 ATCC 74329, *Sporotichum pruinosum* FD 29586 ATCC 74328, *Sporotrichum pruinosum* FD 29458 ATCC 74330 and *Phanerochaete chrysosporium* LN 3576 ATCC 74326 and isolating said compound of formula (I).

2. The process of claim 1 further comprising fermenting said culture in an aqueous nutrient medium comprising assimilable sources of carbon, nitrogen and salt.

3. The process according to claim 2 wherein said fungus is *Sporotrichum pruinosum* FD 29585 ATCC 74327.

4. The process according to claim 2 wherein said fungus is *Sporotrichum pruinosum* FD 29454 ATCC 74329.

5. The process according to claim 2 wherein said fungus is *Sporotrichum pruinosum* FD 29586 ATCC 74328.

6. The process according to claim 2 wherein said fungus is *Sporotrichum pruinosum* FD 29458 ATCC 74330.

7. The process according to claim 2 wherein said fungus is *Phanerochaete chrysosporium* LN 3576 ATCC 74326.

8. A process for preparing the compound of formula (II)

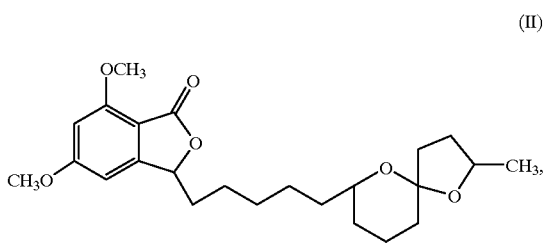

(II)

comprising fermenting a culture of a fungus selected from the group consisting of *Sporotrichum pruinosum* FD 29585 ATCC 74327, *Sporotrichum pruinosum* FD 29454 ATCC 74329, *Sporotrichum pruinosum* FD 29586 ATCC 74328 and *Phanerochaete chrysosporium* LN 3576 ATCC 74326 and isolating said compound of formula (II).

9. The process according to claim 8 wherein said fungus is *Sporotrichum pruinosum* FD 29585 ATCC 74327.

10. The process according to claim 8 wherein said fungus is *Sporotrichum pruinosum* FD 29454 ATCC 74329.

11. The process according to claim 8 wherein said fungus is *Sporotrichum pruinosum* FD 29586 ATCC 74328.

12. The process according to claim 8 wherein said fungus is *Phanerochaete chrysosporium* LN 3576 ATCC 74326.

13. The process of claim 2, wherein said nutrient medium further comprises $H_3BO_3$, $(NH_4)_6Mo_7O_{24}$ $4H_2O$ ) or a combination thereof.

* * * * *